US00PP14325P29

(12) United States Plant Patent
Hanes

(10) Patent No.: US PP14,325 P2
(45) Date of Patent: Nov. 25, 2003

(54) PETUNIA PLANT NAMED 'JAM HOPINK'

(50) Latin Name: *Petunia hybrida*
Varietal Denomination: Jam Hopink

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,102
(22) Filed: Mar. 13, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by red-purple colored flowers, compact habit and good basal branching.

1 Drawing Sheet

Genus and species: *Petunia hybrida.*
Variety denomination: 'Jam Hopink'.

BACKGROUND OF THE NEW PLANT

The present invention comprises a new and distinct cultivar of petunia, botanically known as *Petunia hybrida,* and hereinafter referred to by the cultivar name 'Jam Hopink'. The new cultivar is asexually reproduced from vegetative cuttings and tissue culture resulting from the cross of the seed/pod parent 99-132-1, a pink proprietary line that is unnamed and unpatented ×99-87-2, a double white proprietary line that is unnamed and unpatented.

'Jam Hopink' is a product of a planned breeding program intended to create new petunia plants with Red-Purple colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a two-year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The Photograph shows the mature flowers.

DESCRIPTION OF THE NEW CULTIVAR

The following detailed descriptions set forth the distinctive characteristics of 'Jam Hopink'. The data, which defines these characteristics, were collected from asexual reproductions carried out in Gilroy, Calif. The plant history was taken on 8 months old plants grown in one-gallon pots in fall/winter season, in a poly-covered greenhouse under 2–4 hours supplemental light and color readings were taken in the greenhouse in the winter season under natural light.

Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Petunia hybrida.*
*Commercial.*—Petunia.
Form: Semi upright and decumbent.
Growth and branching habit: Good vigorous habit, well-branched, full plant.
Height: From soil level to top of blooms: Approximately 10–15 cm.
Width: Approximately 55–65 cm including flowers.
Time to produce a finished flowering plant: 9–11 weeks.
Outdoor plant performance: Full sun, free- flowering through the summer, some heat tolerance. Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 5.0–6.0 cm.
Width: 4.2–4.4 cm.
Leaf blade shape: Ovate.
Leaf margin: Entire.
Apex aspect: Acute.
Base aspect: Acuminate.
Leaf color: Upper side; between RHS 137A/B (green); Underside; RHS 138A (green).
Texture: Glandular hairs.
Venation: Palmate.
Venation color: Green RHS 144B (yellow-green).
Petiole length: 0.3–0.4 cm.
Petiole width: 0.3 cm.
Petiole color: RHS 144B (yellow-green).
Petiole texture: Glandular hairs of various sizes.

THE STEM

Length: 50–60 cm.
Diameter: 0.3–0.5 cm.
Internode length: 2.0–4.0 cm.
Color: RHS 145B (yellow-green).
Texture: Much glandular hair of various sizes.
Stem anthocyanin: None.
Peduncle color: RHS 144A (yellow-green).
Peduncle length: 6.0–6.5 cm.
Peduncle diameter: 0.15–0.2 cm.
Peduncle texture: Many glandular hairs of various sizes.

THE BUD

Shape: Oblong.
Diameter: 0.5–0.6 cm.
Length: 1.5–3.0 cm.
Color at tight bud: RHS 160B (greyed-yellow).

THE FLOWER

Blooming habit: Continuous all through the growing season. Good floriferousness.
Inflorescence type: Flowers solitary in upper leaf axis.
Young flower color: RHS N66B (red-purple) but a little lighter.
Young flower floret diameter: 5.3–5.5 cm.
Mature flower color: Front side, between RHS N74A (red-purple), with RHS 184C (greyed-purple) mid vein. Underside, RHS 75C (purple) with RHS N144C (yellow-green) mid vein.
Corolla tube color inside: Base color RHS 155C with mid-veining RHS 152B (yellow-green) with faint minor veins of RHS 152C (yellow-green) & RHS 166D (greyed-orange).
Corolla tube length: 2.3–2.5 cm (Calyx to the petal flare).
Corolla outside texture: Long glandular hairs.
Floret form and number of petals: Funnel form, 5 lobed petals (single type) fused at base.
Flower (limb) diameter: 5.5–6.0 cm.
Petal apex shape: Cuspidate.
Petal margin: Entire.
Petal waviness (ruffle of petal): Weak.
Petal lobation: Moderate.
Petal texture: Papillose.
Calyx: 5 deeply lobed sepals, fused at base.
Sepal color: RHS 137B (green).
Sepal length: 1.7–2.0 cm.
Sepal width: 0.4–0.7 cm.
Sepal shape: Oblong.
Sepal apex: Obtuse.
Sepal texture: Glandular hairs of various sizes.
Lastingness of individual blooms: 4–7 days.
Fragrance: None.

THE REPRODUCTIVE ORGANS

Stamens: Five, 2 taller and 3 shorter.
Filament color: RHS 155A (white).
Pollen color: RHS 11C (yellow).
Pistil: One.
Stigma: RHS 145A (yellow-green).
Style color: RHS 145C (yellow-green).
Fruit seed set: Not observed.

DISEASE AND INSECT RESISTANCE

Not observed.

COMPARISON WITH KNOWN CULTIVARS

Compared to its female parent 99-132-1 as follows: 'Jam Hopink' has a darker pink flower color is more trailing and earlier to flower.

Compared to its male parent 99-87-2 as follows: 99-87-2 is a white flower with double flower form and the hybrid is red-purple with a single flower. The male is more upright in plant habit than 'Jam Hopink'.

I claim:

1. A new and distinct petunia plant as shown and described herein.

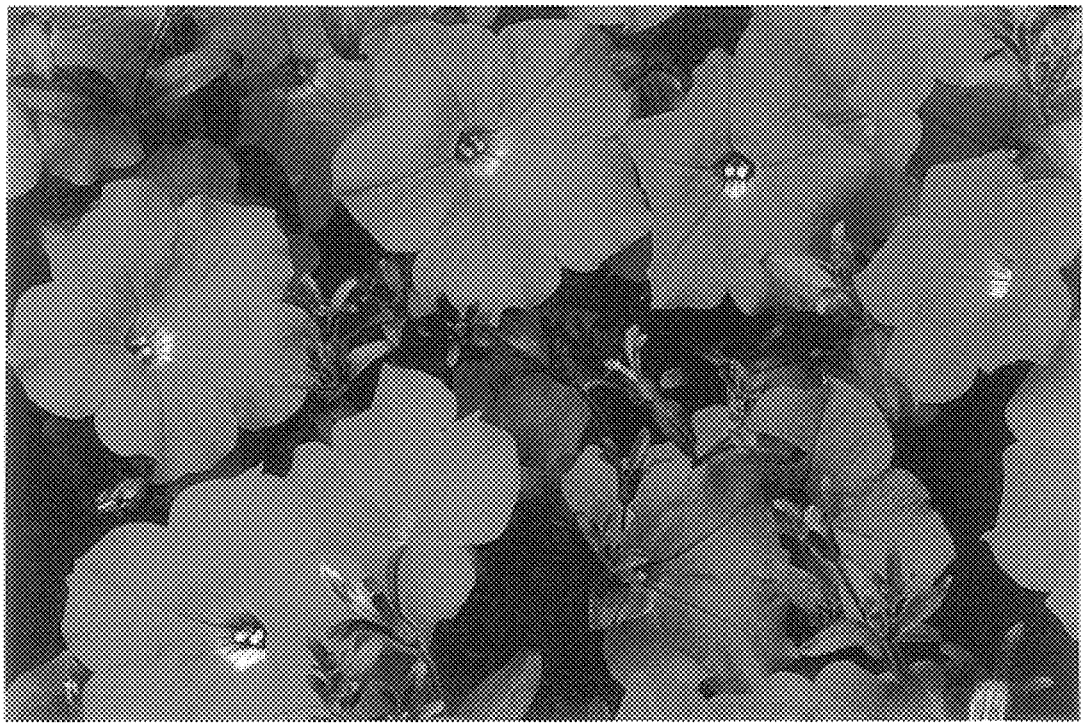

* * * * *